ary Examiner—Frank Spear

United States Patent [19]

Hu et al.

[11] Patent Number: 5,151,189
[45] Date of Patent: Sep. 29, 1992

[54] CATIONIC CHARGE MODIFIED MICROPOROUS MEMBRANE

[75] Inventors: Ho-Pin Hu; Inessa Katsnelson; Alan Sellinger, all of Ann Arbor, Mich.

[73] Assignee: Gelman Sciences, Inc., Ann Arbor, Mich.

[21] Appl. No.: 583,640

[22] Filed: Sep. 17, 1990

[51] Int. Cl.$^5$ .............................................. B01D 67/00
[52] U.S. Cl. ..................................... 210/635; 210/645; 210/490; 210/500.39; 521/27; 204/299 R
[58] Field of Search ............... 210/635, 645, 198.3, 210/502.1, 500.42, 490, 500.39, 500.43; 264/41, 49; 427/245; 422/69, 70; 521/27; 204/182.8, 299 R

[56] References Cited

U.S. PATENT DOCUMENTS

| | | | |
|---|---|---|---|
| 4,007,113 | 2/1977 | Ostreicher | 210/23 R |
| 4,473,474 | 7/1984 | Ostreicher | 210/636 |
| 4,473,475 | 9/1984 | Barnes et al. | 210/638 |
| 4,512,896 | 4/1985 | Gershoni | 210/635 |
| 4,523,995 | 6/1985 | Pall et al. | 210/504 |
| 4,601,828 | 7/1986 | Gershoni | 210/635 |
| 4,604,208 | 8/1986 | Chu et al. | 210/636 |
| 4,673,504 | 6/1987 | Ostreicher et al. | 210/500.22 |
| 4,708,803 | 11/1987 | Ostreicher et al. | 210/650 |
| 4,743,418 | 5/1988 | Barnes, Jr. et al. | 264/48 |
| 4,900,449 | 2/1990 | Kraus et al. | |
| 4,964,990 | 10/1990 | Kraus et al. | 210/500.42 X |

FOREIGN PATENT DOCUMENTS 0347755 6/1989 European Pat. Off. .

Primary Examiner—Frank Spear
Attorney, Agent, or Firm—Krass & Young

[57] ABSTRACT

Cationic charge modified microporous hydrophilic membranes are provided, as well as preparation of the same by post-treatment. Typically, as an illustration, a microporous hydrophilic membrane substrate which contains non-leachable polymeric additive having functional groups is treated in an alkaline solution for simultaneous or sequential reaction with 1) a primary charge modifying agent which is an epichlorohydrin modified polyamine, and 2) a secondary polymeric charge modifying agent containing a fixed formal positive charge (or for reaction with the primary charge modifying agent alone); then cured at elevated temperature; and finally washed and dried. The cationically charged microporous membranes are used in various applications such as the filtration of fluids and the macromolecular transfer from electrophoresis gels.

38 Claims, 4 Drawing Sheets

CATIONIC CHARGE MODIFIED MICROPOROUS MEMBRANE

FIELD OF THE INVENTION

This invention relates to novel cationic charge modified microporous hydrophilic membranes useful for filtration of fluids, macromolecular transfers, electrophoresis, blotting methods, and the like. More particularly, this invention relates to cationic charge modified microporous membrane media of the type used in medical, genetic and biochemical research and in the food and wine, cosmetics, biotechnology, pharmaceutical, and electronics industries.

BACKGROUND OF THE INVENTION

Microporous membranes are usually defined as thin walled structures having an open spongy morphology with a narrow pore size distribution. The mean pore sizes for microporous membranes typically range between 0.01 μm and 10 μm. Traditionally, microporous membranes are used to remove fine particulate matter such as dust and bacteria from liquids and gases. A microporous membrane can achieve the clarification by different mechanisms. For example, particulates can be retained by microporous membranes through physical sieving of all particulates larger than the pore size of the membranes. In this mechanism, filtration efficiency is governed by the relative size of the particulates and membrane pore size. Due to the increasing need for removing finer and finer particulates, particularly in pharmaceutical and electronic industries, microporous membranes with very small pore size are required to achieve effective filtration. However, membranes with such a small pore size tend to have some undesirable characteristics such as high pressure drop across tee membrane, decreased flow rate, reduced particulate capture capacity, and shortened membrane life.

Another mechanism in which a microporous membrane can remove suspended particulate materials is the electrokinetic capture mechanism. This is achieved by imparting an appropriate zeta potential to the membranes' internal and external surfaces. In principle, when a charged surface is immersed in an aqueous medium or other polar medium, a charge double layer will form at the solid-liquid interface. One component of the double layer is the charged solid surface, and the other layer is the counter ionic region in the medium. When the solid and liquid are set in relative motion, a potential difference will develop between the mobile and immobile regions in the medium close to the surface. This potential, the so-called "zeta potential" is given for a fluid flowing through a charged porous membrane by the equation:

$$\zeta = \frac{4E\pi\eta K}{PD}$$

where $\zeta$ is the zeta potential, $\eta$ is the solution viscosity, D is dielectric constant, E is the streaming potential, P is the driving pressure and K is the specific conductance of the solution.

The zeta potential can be either positive or negative depending on the charge of the solid surface. Most suspended particulates which are commonly subjected to removal by filtration have a negative zeta potential. Therefore, such particulates will be readily adsorbed or attracted by solid surfaces that have positive zeta potentials. Based on this, applying a positive zeta potential to the available surface of a microporous membrane will greatly improve the particulate capture capacity of the membrane. This is true even for particulates whose size is much smaller than the membrane pore size. As a result, a high fluid flow rate through the membrane can be maintained using this concept and yet particulate capture by the membrane is much more efficient than indicated by the rated pore size of the membrane.

Attempts to enhance flow rates and to increase membrane life using cationically charged membranes have been made for a number of years. For example, the U.S. Pat. Nos. 4,007,113, 4,473,474, 4,673,504, and 4,708,803 to Ostreicher et al. describe the use of a charge modified filter and process for making the same. U.S. Pat. No. 4,473,475 to Barnes et al. also disclose a cationically charged microporous membrane and its usage. U.S. Pat. No. 4,523,995 to Pall et al. and U.S. Pat. No. 4,604,208 to Chu et al. are other examples of charge modified microporous membranes.

Each of the above mentioned patents is limited to the use of charge modified membranes in filtration applications. However, such charge modified microporous membranes can be used for macromolecular transfer application (e.g., DNA Southern blot) and have already been suggested in U.S. Pat. Nos. 4,512,896 and 4,601,828 to Gershoni and in European patent application 0347755 to Pluskal et al.

The term "macromolecular transfer" as used herein refers to processes for transferring biological macromolecules such as nucleic acids and proteins from electrophoresis gels to some type of immobilizing matrix. Of particular importance is nucleic acid blotting, such as DNA blotting. A variety of DNA blotting techniques have been developed in the past. Among them, the most common is referred to as "Southern blotting" in which DNA fragments are separated by chromatographic techniques and then denatured while still in the gel. The gel is neutralized and placed over wicking papers which are in contact with buffer held in a buffer reservoir. The blotting membrane is then placed on top of the gel. As the buffer flows into the gel, DNA is eluted and binds to the blotting membrane, thereby transferring the DNA fragment pattern onto the blotting membrane. The fragment pattern can finally be detected using hybridization techniques employing labeled nucleic acids which are complementary to the specific bound fragments.

DNA blotting membranes presently available are limited to nitrocellulose, charged nylon, charged polyvinylidine difluoride, and activated papers derivatized with diazo containing compounds.

SUMMARY OF THE INVENTION

The present invention, as indicated, concerns cationic charged modified microporous hydrophilic membranes containing a polymeric substrate and a polymeric additive and process for preparing the same. The substrate comprises a primary charge modifying agent containing high molecular weight polymer exposed at the internal and external microporous surfaces. The exposed modified polymer is chemically grafted onto the membrane substrate and therefore is permanently charged. The polymeric additive is the presumed grafting site.

DETAILED DESCRIPTION OF THE INVENTION

Figure 1:
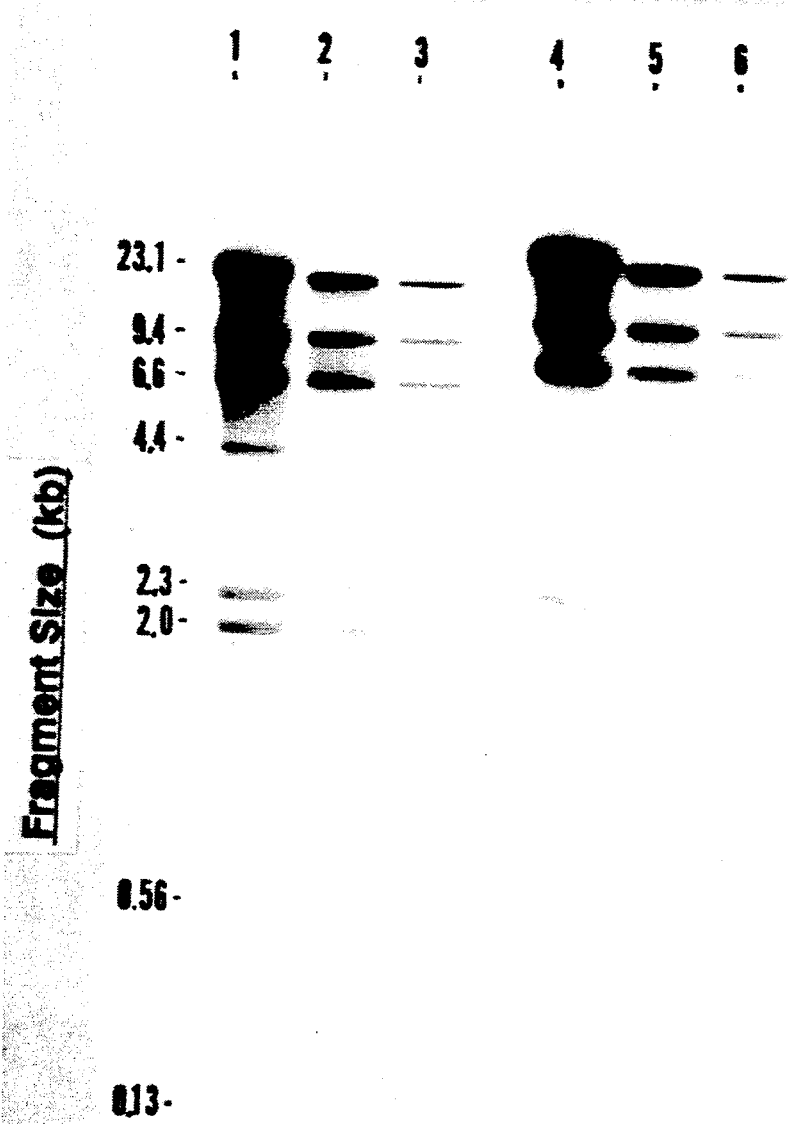
FIG. 1 is an autoradiogram by Southern blot analysis comparing a charged nylon membrane to a charged polyethersulfone membrane using optimal conditions for each membrane in DNA blotting. Lines 1, 2 and 3 were associated with a cationically charged polyethersulfone membrane under alkaline conditions and lanes 4, 5 and 6 were associated with a competitive cationically charged nylon membrane under neutral conditions. The DNA loading was 1 μg for lanes 1 and 4, 0.1 μg for lanes 2 and 5, and 0.01 μg for lanes 3 and 6.

The cationically charged substrates of this invention comprise hydrophilic, microporous membranes which have been charge modified with fixed formal charge groups containing a net positive charge. The term "microporous membrane" as used herein defines a membrane having an average pore size of at least 0.05 μm or a water bubble point (WBP) of less than 120 psi. A maximum pore size of membrane useful for this invention is about 10 μm.

The preparation of cationically charged microporous membranes described in this invention is based on a post-treatment process. The membrane substrate suitable for the post-treatment must contain at least one non-leachable polymeric additive (preferably at least 2 Wt % with respect to the major matrix polymer in the microporous membrane). The additive enhances hydrophilicity and has functional groups latently reactive with epoxy groups (or the precursor of epoxy groups). An example of a suitable substrate membrane is described in U.S. Pat. No. 4,900,449. This membrane contains polyvinylpyrrolidone and polyethylene glycol as non-leachable, intrinsic wetting agents. The principle chemistry in this invention is based on the chemical grafting of a primary charge modifying agent to the polymeric additive or additives in the membrane substrate. The primary charge modifying agent must contain epoxy groups and/or the precursor of epoxy groups or other functionality which can chemically react with hydroxyls, amines, and other active functional groups; and must contain polyamines which can chemically react with other electrophile containing compounds and impart the positive charge. Polyethyleneimine - epichlorohydrin modified resin which is available commercially as SC-86X (Trademark of Morton-Thiokol, Chicago, Ill.) is the preferred primary charge modifying agent. This resin has the chemical structure shown below.

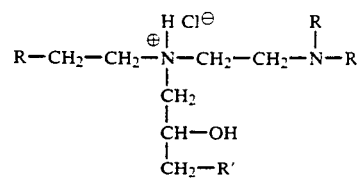

where R is hydrogen or a continuation of the polyamine chain and R' represents —OH or —Cl. The preferred primary charge modifying agent used in this invention is a water soluble polymer. Other polymers having chemical properties similar to the preferred primary charge modifying agent can also be used.

Since the protonated amino group in the preferred charge modifying agent is not a fixed quaternized amine group, and is sensitive to the variance of environmental pH, a secondary charge modifying agent containing fixed formal positive charge and some functional groups which can chemically react with the primary charge modifying agent can be added according to a preferred embodiment to increase the charge capacity and to decrease the pH dependence of the final cationically charged membrane. Preferably, the secondary charge modifying agent is a) partially phosphinated polyvinylbenzyl chloride synthesized by the reaction of polyvinylbenzyl chloride with trialkyl (or triaryl) phosphine, or b) quaternized poly(dimethylamine-co-epichlorohydrin). The latter chemical is commercially available from Scientific Polymer Products, Inc., Ontario, N.Y. The chemical structure of the preferred secondary charge modifying agents is as follows:

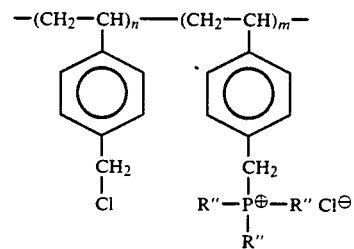

where m and n are integers indicating the polymer length and R" independently represents lower alkyl or aryl (preferably phenyl); and

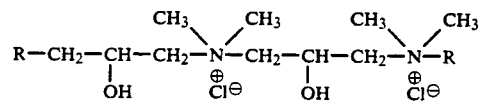

where R is a continuation of the polymer chain.

Other secondary charge modifying agents which chemically behave similarly to the aforementioned secondary charge modifying agents can also be used in this invention. For example, ionic species other than phosphonium ions in the partially phosphinated polyvinylbenzyl chloride such as ammonium, sulfonium, or the like which form fixed formal positive charge groups are also suitable in this invention.

The process of preparing the cationically charged membrane in this invention typically includes the following steps:

1. Soaking the microporous membrane in an aqueous solution (or ethanol/water solution in the ratio of 10 Wt % to 30 Wt %) preferably containing 3 Wt % to 7 Wt % of primary charge modifying agent, zero Wt % to 6 Wt % of secondary charge modifying agent, 0.5 Wt % to 3 Wt % of potassium hydroxide (pH=9 to 11), and zero Wt % to 2 Wt % tetrabutylammonium bromide for a sufficient time, e.g., a few seconds, at ambient temperature to wet out the membranes completely;
2. Removing the membranes from the treating solution, wiping off the excess treating solution, e.g., by "squeegee" action using wiper bars, and baking preferably at 110° C. to 140° C. for 20 to 40 minutes;
3. Washing the membranes preferably in 90° C. deionized water for 20 minutes, and finally drying preferably at 60° C. to 80° C. for 15 to 20 minutes.

The microporous membranes after the above post-treatment generally have 10% to 25% reduction in water flow rate and 1% to 5% increase in water bubble point as compared with the native untreated membranes. However, the cationically charged microporous membranes so prepared still exhibit excellent hydrolytic stability. For example, these cationically charged membranes will not lose their charge capacity and membrane strength after ethanol-Soxhlet extraction for 3 days, 120° C. autoclaving for 40 minutes, or boiling in DI water for 1 hour.

The reaction mechanism of the preferred post-treatment process described above using the preferred membrane substrate and preferred primary and secondary charge modifying agents, may be proposed as follows.

First, under alkaline condition at elevated temperature, the non-leachable polyvinylpyrrolidone present in the membrane substrate undergoes a ring-opening hydrolysis process to form free amine and carboxyl groups which, in situ, react with epoxy groups of the primary charge modifying agent derived from the epichlorohydrin moieties. Simultaneously, the hydroxy groups of non-leachable polyethylene glycol present in the membrane substrate also chemically react with the epoxy groups of the modifying agent to generate the ether linkage. These two reactions result in the charge modifying agents being grafted on the membrane substrate. Further reactions including the self-crosslinking of the primary charge modifying agent under alkaline conditions and the reaction of the primary charge modifying agent with the secondary charge modifying agent may also occur simultaneously. As a result, a cationically charged membrane is produced through this complicated grafting/crosslinking process. While the above is a plausible mechanism for the grafting, it has not been rigorously proven so that this invention is not limited to this or any other theory.

On the basis of this proposed mechanism, the major polymer (e.g., polyethersulfone) in the membrane substrate does not play any role in the grafting reaction. This has been proved by control experiments in which a hydrophobic polyethersulfone membrane prepared from a polymer mix containing no active polymeric additives (polyethylene glycol and polyvinylpyrrolidone) was used in the post-treatment process. The result clearly indicated that no detectable charge was present on the membrane after post-treatment. This demonstrates that the presence of active additives in the membrane is essential for the preparation of cationically charged membranes using the post-treatment process disclosed in this invention.

The cationically charged microporous membranes produced by the described process using quaternized poly(dimethylamine-co-epichlorohydrin) as the secondary charge modifying agent wet instantly in water. However, the charged membranes prepared from the treating solution containing partially phosphinated polyvinylbenzyl chloride (assuming 90% conversion from polyvinylbenzyl chloride to phosphinated polyvinylbenzyl chloride based on the stochiometric ratio in the conversion reaction) do not wet instantly when immersed in aqueous solution. Therefore, these latter membranes must be wetted prior to use (such as use in macromolecular blotting applications) in a water miscible organic solvent which may be either neat or in aqueous solution. The water miscible solvent may be an alcohol (e.g., methanol, ethanol, or isopropanol).

TESTING METHODS

The following are descriptions of tests performed in the Examples.

Water Bubble Point

This common test for microporous membranes is a measurement of the largest pores in a membrane. It consists of expelling water from a water wetted membrane by air pressure. Pore size and the pressure necessary to remove water from that pore are related by:

$$D = \frac{B\gamma\cos\Theta}{P}$$

where P is the pressure, $\Theta$ is the liquid-solid contact angle between the membrane material and water, $\gamma$ is the liquid-air surface tension, D is pore diameter, and B is a constant.

Water Flow Rate

Water flow rate is the flow rate of water passing through the membrane of given dimension, and commonly expressed in seconds/100 mL of water at a given pressure.

Dye Adsorption

Membrane surfaces which have a positive zeta potential will adsorb negatively charged organic dyes. This can be used to semi-quantify the charging efficiency of charged membrane.

Ion Exchange Capacity

The ion exchange capacity is determined as meq per gram of charged membrane by the titration method.

Endotoxin Removal Efficiency

Endotoxin removal efficiency is determined by challenging the membrane by a known concentration and volume of purified endotoxin and measuring the endotoxin in the permeate.

Extractables

The amount of extractables is determined by boiling the membrane in water for one hour and measuring the weight loss.

Latex Sphere Retention

Latex sphere retention measures the particulate removal efficiency of microporous membranes. Briefly, a monodisperse suspension of polystyrene latex with well-characterized particle size is used to filter through a membrane under vacuum. The aliquots of filtrate are then analyzed by UV-Vis spectrophotometer at specific wavelength.

EXAMPLES

EXAMPLE 1 - Preparation of 0.2 μm Polyethersulfone Membrane

Polyethersulfone (Victrex ® TM 5200 available from ICI), dimethylformamide, and polyethyleneglycol 400 were mixed in the ratio of 13:18:69. The mix was stirred to homogeneity and cast at 10-12 mil on glass or stainless steel. Then, the polymer solution was subjected to 60-70% relative humidity ambient air until it became opaque. The membrane was immersed in water to complete coagulation and leach out excess solvent for 2-12 hours, and finally dried at 70° C.

The membrane obtained was instantly water wettable and exhibited 100% bacteria retention when challenged with $10^7/cm^2$ of *Pseudomonas diminuta*. The membrane had the following characteristics:

| | |
|---|---|
| Water Bubble Point | 56 psi |
| Water Flow Rate | 22 seconds/9.62 cm$^2$ - 100 mL at 10 psi |

Elemental analysis of the membrane obtained by combustion method indicated the absence of dimethylformamide in the membrane. Nuclear Magnetic Resonance of the dissolved membrane showed that it contained 5 Wt % of polyethylene glycol 400. After Soxhlet extraction using ethanol for two days, this membrane lost its hydrophilicity. Nuclear Magnetic Research of such dissolved membrane showed that it still contained 2 Wt % of polyethylene glycol 400.

EXAMPLE 2 - Preparation of 0.2 μm Hydrophobic Polyethersulfone Membrane

Polyethersulfone, dimethylforamide, and sodium bicarbonate were mixed in the ratio of 13.3:53.4:33.3. The membrane was then made by a procedure similar to that described in Example 1. The membrane so obtained however was completely hydrophobic. The membrane characteristics were:

| | |
|---|---|
| Water Bubble Point* | 16 psi |
| Water Flow Rate* | 120 seconds/9.62 cm$^2$ - 100 mL at 10 psi |

EXAMPLE 3 - Preparation of 0.2 μm Intrinsically Hydrophilic Polyethersulfone Membrane A casting solution was prepared by mixing polyethersulfone, polyvinylpyrrolidone (available from GAF Corporation, Cincinnati, Ohio) polyethyleneglycol, dimethylformamide, in the ratio of 13:0.2:66.8:20. The membrane was cast and set as in Example 1. The membrane so obtained was spontaneously water wettable. After Soxhlet extraction using ethanol for 3 days, 100° C. water boiling for 30 minutes, or 121° C. autoclaving for 45 minutes, the membrane did not loose its instant water wettability and performance. The membrane performance was:

| | |
|---|---|
| Water Bubble Point | 58 psi |
| Water Flow Rate | 21 seconds/9.62 cm$^2$ - 100 mL at 10 psi |

When challenged with $10^7/cm^2$ of *Pseudomonas diminuta*, the membrane exhibited 100% bacteria retention. Elemental analysis of such membrane showed that it contained 1% polyvinylpyrrolidone.

EXAMPLE 4 - Preparation of 0.2 μm Intrinsically Hydrophilic Membrane

A polymer casting solution was prepared by mixing polyethersulfone, polyvinylpyrrolidone, polyethyleneglycol, and dimethylformamide in the ratio of 13:2:65:20. The membrane was cast and set as in Example 1. The membrane so prepared was instantly water wettable and did not change its hydrophilicity and membrane performance after ethanol Soxhlet extraction for 3 days. Elemental analysis of the membrane prepared indicated that it contained 2% polyvinylpyrrolidone which was about 1% higher than the membrane made in Example 3.

EXAMPLE 5 - Preparation of 0.45 μm Intrinsically Hydrophilic Polyethersulfone Membrane A hydrophilic polyethersulfone membrane was made in a process essentially the same as that described in Example 3 except that polyethersulfone, polyvinylpyrrolidone, polyethyleneglycol, and dimethylformamide in the ratio of 13:0.2:58.8:28 were used to prepare the casting solution. The membrane so prepared had the following characteristics:

| | |
|---|---|
| Water Bubble Point | 33 psi |
| Water Flow Rate | 11 seconds/9.62 cm$^2$ - 100 mL at 10 psi |

The membrane obtained had 100% bacteria retention when challenged with $10^7/cm^2$ of *Serratia marcescens*.

EXAMPLE 6 - Preparation of Partially Phosphinated Polyvinylbenzyl Chloride Resin To a 1000-mL round-bottomed flask equipped with a mechanical stirrer and a condenser was added 76 g of polyvinylbenzyl chloride resin (0.5 eq), 118 g of triphenyl phosphine (0.45 eq), and 600 mL of dimethylformamide. This solution was allowed to stir at 75° C. for 16 hours. After cooling, the solution was poured into copious amounts of acetone with vigorous agitation to precipitate the resultant polymer. The powder polymer was isolated by simple filtration and washed with acetone, and finally dried in vacuo at 40° C. for 2 days.

The resultant resin was not soluble in water. However, it was readily soluble in neat methanol or 10% methanol-water mixture.

EXAMPLE 7 - Preparation of 0.2 μm Cationically Charged Membrane

The membrane made in Example 3 was placed in an aqueous solution containing 4% polyethyleneimine-epichlorohydrin (SC-86X available from Morton-Thiokol), 2% potassium hydroxide, and 1% tetrabutylammonium bromide for a few seconds, and then was removed from the treating solution. Excess polymer solution was wiped off from the membrane using squeegee bars. The membrane was then baked in a vented oven at 140° C. for 20 minutes. After baking, the membrane was washed with DI water at 90° C. for 20 minutes, and finally dried at 70° C. for 20 minutes. The membrane so prepared had cationic charge evidenced by anionic dye adsorption. The dye adsorption capacity and the membrane properties such as water bubble point and water flow rate did not change after ethanol-Soxhlet extraction and autoclaving.

EXAMPLE 8 - Preparation of 0.2 μm Cationically Charged Membrane

The membrane made in Example 3 was soaked in an aqueous solution containing 2% polyethyleneimine-epichlorohydrin (SC-86X available from Morton-Thiokol), 2% quaternized poly(dimethylamine-co-epichlorohydrin) (available from Scientific Polymer Products, Inc.) 2% potassium hydroxide, and 1% tetrabutylammonium bromide for a few seconds to completely wet the membrane, and then was removed from the treating solution. Excess resin solution removed by "squeegee" action using wiper bars. The membrane was then baked in a vented oven at 140° C. for 15 minutes. After curing, the membrane was washed with DI-water at 90° C.C. for 20 minutes, and finally dried at 70° C. for 15 minutes or longer. The membrane so prepared showed a strong evidence of presence of cationic charge. The characteristics of cationically charged membrane so prepared (water bubble point, water flow rate, dye adsorption and others) did not change after ethanol-Soxhlet extraction, autoclaving and boiling processes. This suggests that the membrane after the aforementioned post-treatment is indeed permanently charged.

EXAMPLE 9 - Preparation of 0.45 μm Cationically Charged Membrane

The post-treatment process was conducted in the same manner as described in Example 8 except that 0.45 μm membrane made in Example 5 was used as membrane substrate.

EXAMPLE 10 - Preparation of 0.2 μm Cationically Charged Membrane

The membrane substrate made in Example 3 was used in this Example. In addition, ethanol-mixture (20:80 in weight ratio) was used as solvent to prepare the treating solution. The treating solution was composed of 2% polyethyleneimine-epichlorohydrin, 2% partially phosphinated polyvinylbenzyl chloride, 2% potassium hydroxide, and 1% tetrabutylammonium bromide. The actual post-treatment processes were carried out in a manner identical to those described in Example 8.

EXAMPLE 11 - Preparation of 0.45 μm Cationically Charged Membrane

A post-treatment was conducted under the same conditions as those of Example 10 except that 0.45 μm membrane made in Example 5 was used as the membrane substrate.

EXAMPLE 12 - Control Experiments to Corroborate the Necessity of Active Additives in Membrane Substrate to Prepare Cationically Charged Membrane

Control 12-A

An aqueous solution containing 15% polyvinylpyrrolidone and 2% potassium hydroxide was first boiled for 40 minutes to achieve the base hydrolysis of polyvinylpyrrolidone. The boiled polymer solution had a slightly brown color and showed a remarkably higher viscosity than the non-boiled polymer solution, most likely indicating the occurrence of hydrolysis of polyvinylpyrrolidone after such treatment. The boiled polymer was then cast on a glass plate and cured at 140° C. for 30 minutes to form a brown transparent film. The resultant film was however readily soluble in water as the native polyvinylpyrrolidone film was. This result proved that there was no self-crosslinking of hydrolyzed polyvinylpyrrolidone (or native polyvinylpyrrolidone) under the above conditions.

Control 12-B

An aqueous solution containing 10% polyethyleneimine-epichlorohydrin and 3% potassium hydroxide was cast on a glass plate, and then cured at 140° C. for 30 minutes. The film so formed was completely disintegrated into broken fragments after immersion in water at ambient temperature. This confirms that the self-crosslinked polyethyleneimine-epichlorohydrin is not hydrolytically stable.

Control 12-C

An aqueous solution containing 8.8% polyvinylpyrrolidone, and 1% potassium hydroxide was first boiled for 1 hour to accomplish the base hydrolysis of polyvinylpyrrolidone. After cooling the solution to ambient temperature, 7% polyethyleneimine-epichlorohydrin (based on the total weight of final solution) was added with gentle agitation. The final polymer solution was then cast on a glass plate and cured at 140° C. for 30 minutes to form a film. Unlike the films obtained in control 12-A and control 12-B, the film so formed still retained its integrity even after soaking in water at ambient temperature for 24 hours. This demonstrated that the reaction between polyethyleneimine-epichlorohydrin and hydrolyzed polyvinylpyrrolidone occurred, and the resultant film was hydrolytically stable.

Control 12-D

The Soxhlet extracted membrane made in Example 1 was post-treated under conditions similar to those described in Example 8. After post-treatment, the membrane exhibited cationic charge characteristics even after ethanol Soxhlet extraction for 24 hours. This indicated that the non-leachable active additives (polyethylene glycol 400) in the membrane substrate indeed reacted with charging agents in the treating solution.

Control 12-E

The hydrophobic membrane made in Example 2 was subjected to the post-treatment process as described in Example 8 except that it was prewetted by ethanol. Consequently, the treated membrane was still hydrophobic and showed no sign of presence of cationic charge.

Control 12-F

The membrane made in Example 4 was post-treated according to the procedures described in Example 8. However, the charged membrane so prepared had a slightly higher charge capacity than the charged membrane made in Example 8. This further corroborates that the success of preparing cationically charged membranes using the disclosed method herein is indeed dependent upon the active additives in the membrane substrate. In a certain range, the charge capacity of the cationically charged membranes is a function of the quantity of active additives in the membrane substrate.

EXAMPLE 13 - Anionic Dye Adsorption of Membrane

Dye adsorption testing was done with dilute aqueous solution (11 ppm) of a negatively charged Metanil Yellow. The solution was filtered through the test samples (47 mm in diameter) at 10 psi and the end point of testing was visually determined and expressed in terms of volume of dye solution when the filtrate penetrating through membrane samples became very light yellow. The membrane samples used in the test and the following tests had a thickness of 5.4 mil±0.6 mil. The accuracy of this dye adsorption test was ±15 mL of dye solution. The dye adsorption capacities of membrane samples are set out in Table I below.

TABLE I

| Membrane Sample of Example # | 11 ppm Metanil Yellow Dye Adsorption (mL) |
|---|---|
| 1 | 15 |
| 2 | 20 |
| 3 | 20 |
| 4 | 20 |
| 5 | 15 |
| 8 | 350 |
| 9 | 230 |
| 11* | 300 |
| 12-D | 55 |
| 12-E | 15 |
| 12-F | 500 |

*This membrane was prewetted in ethanol prior to the dye adsorption test.

EXAMPLE 14 - Measurement of Membrane Extractables

The degree of extractables of hydrophilic membranes was determined by pre-weighing the dry membrane samples, then by boiling them in DI-water for 1 hour. After completely drying, the membrane samples were weighed again. The degree of membrane extractables is expressed in terms of percentage of weight loss and shown in Table II below.

TABLE II

| Membrane Sample of Example # | Extractables % |
|---|---|
| 3 | 0.8 |
| 4 | 0.9 |
| 5 | 0.7 |
| 7 | 0.6 |
| 8 | 0.7 |
| 9 | 0.8 |

EXAMPLE 15 - Ion Exchange Capacity of Cationically Charged Membrane

To measure ion exchange capacity, 47 mm discs of membrane samples were soaked in 100 mL of 0.1M HCl for 5 minutes followed by DI water leaching until the water had a pH about 7. After drying of 70° C. for 2 hours, the membrane samples were placed in 100 mL of DI water, to which 2 mL of $NaNO_3$ solution was added, for 10 minutes. Then 51 mL of this solution was removed and titrated with 0.014M $AgNO_3$ using the indicator solution containing 10 drops of 0.1% dichlorofluorescein and three drops of polyethyleneglycol 400 to stabilize the colloidal silver chloride precipitate. The end point of this test was determined by observation of pink color formation from yellow green color. The ion exchange capacity is finally estimated by simple calculation and expressed as milliequivalent/gram of membrane sample shown in Table III below.

TABLE III

| Membrane Sample of Example # | Ion Exchange Capacity (meg/g) |
|---|---|
| 3 | 0 |
| 7 | 0.69 |
| 9 | 0.51 |
| Control* | 0.94 |

*0.2 um Zetapor membrane available from AMF - Cuno was used for comparison.

EXAMPLE 16 - Endotoxin Removal Efficiency of Membrane

Endotoxin removal efficiency was tested as follows. The membrane samples, all in the form of 47-mm discs were first sterilized by gamma irradiation or autoclave process and then challenged with 10 mL solution of 0.42 EU/mL of purified E. Coli endotoxin. The filtrates were then analyzed by the LAL method. The results are summarized in Table IV below.

TABLE IV

| Membrane Sample of Example # | Endotoxin in Filtrate (EU/mL) |
|---|---|
| 3 | 0.42 |
| 8 | <0.1 |
| 9 | <0.1 |

EXAMPLE 17 - Latex Sphere Retention of Membrane

The particulate removal efficiency of membranes was determined by filtering 30 mL of monodisperse latex sphere (33.3 ppm) suspended in aqueous solution containing 0.1% Triton X-100 at 10 psi. Each 10-mL aliquot of filtrate was collected and analyzed for absorbance by UV-Vis spectrophotometer at 238 nm. The results of these tests are set out in Table V below.

TABLE V

| Membrane Sample of Example # | Sphere Diameter (um) | Latex Sphere Retention (%) | | |
|---|---|---|---|---|
| | | 1st 10 mL | 2nd 10 mL | 3rd 10 mL |
| 3 | 0.065 | 15.2 | 3.1 | 3.4 |
| 8 | 0.065 | 100 | 100 | 100 |

EXAMPLE 18 - Southern Blot Analysis of Cationically Charged Membranes

Southern Blot analysis was performed on the membrane made in Example 9 and on a comparable cationically charged nylon membrane (Genescreen Plus® nylon membrane available from DuPont NEN). It was found that the transfer of DNA to the membrane made in Example 9 was most efficient under alkaline conditions, whereas neutral transfer of DNA was most efficient for the comparable membrane. Therefore, the membranes were compared under ideal conditions for each membrane.

For Southern blots using alkaline transfers, 1,0, 0.1, and 0.01 μg of lambda DNA, Hind III digest (Life Technologies, Gaithersburg, Md.) was electrophoresed on a 0.8% agarose gel using a TAE buffer system as described by Sambrook et al. (Molecular Cloning, Cold Spring Harbor Press, 1989). Following depurination of 250 mM HCl, DNA was transferred to the membrane samples by capillary action using 0.4N NaOH as the transfer buffer. The DNA was then fixed to the membrane samples by baking at 80° C. for 30 minutes.

For neutral transfers, 1.0, 0.1, and 0.01 μg of lambda DNA, Hind III digest, was electrophoresed on a 0.8% agarose gel as described above. The DNA was depurinated and subsequently exposed to 0.4N NaOH/0.6M NaCl for 30 minutes and to 1.5M NaCl/0.5M Tris, pH 7.5 for 30 minutes. Transfer of DNA to the membrane samples was performed by capillary action using 1.5M NaCl/0.15M sodium citrate as the transfer buffer. The membrane samples were then baked at 80° C. for 30 minutes.

A probe was prepared by labelling lambda DNA with deoxycytidine 5'-[a-$^{32}$P] triphosphate (Amersham Corp., Arlington Hts., Ill.) using a random primer extension kit (Life Technologies). Hybridization was allowed to proceed overnight at 65° C. The buffers used for hybridization and washing were previously described (Church and Gilbert, PNAS, 81, 1991, 1984). Southern blots were finally exposed overnight to Kodak X-Omat AR film using Lightening Plus intensifying screens. The results of charged membrane performance are shown in FIG. 1.

EXAMPLE 19 - Southern Blot Analysis of Cationically Charged Membranes

Figure 2:
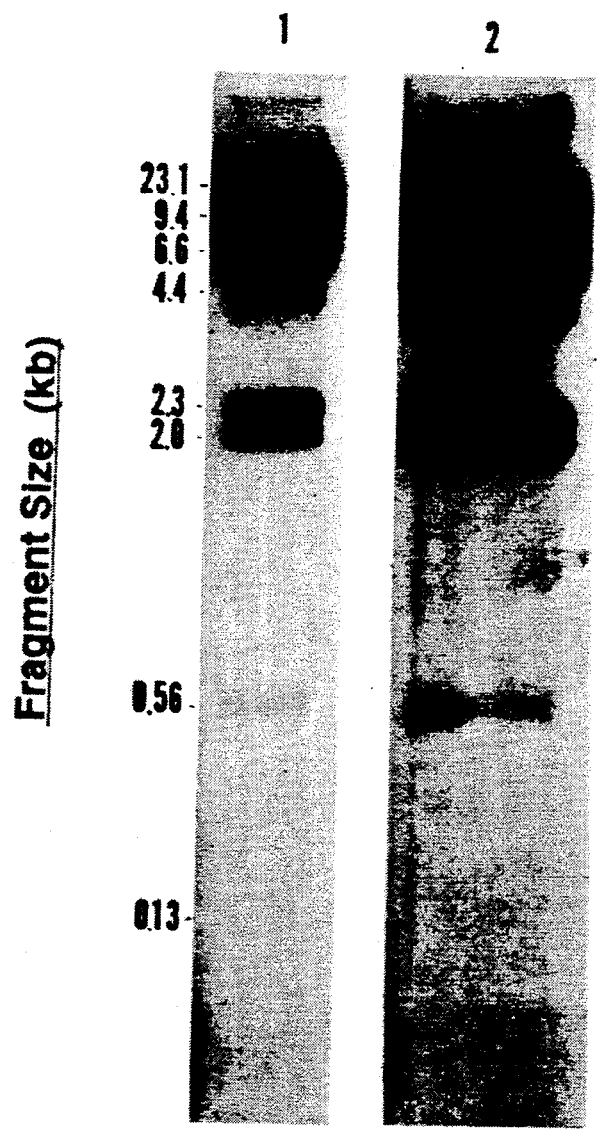
FIG. 2 is an autoradiogram comparing a charged nylon membrane to a charged polyethersulfone membrane using transfer conditions in Southern blotting. Lane 1 was associated with a cationically charged polyethersulfone membrane and lane 2 was associated with a charged nylon membrane; DNA loading was 1 μg for both membranes.

The charged polyethersulfone membrane made in Example 11 and a charged nylon membrane (Genescreen Plus ®) were compared using neutral transfer conditions which were optimal for the charged nylon membrane but not optimal for the charged polyethersulfone membrane. Experimentally, 1.0 μg of lambda DNA, Hind III digest, was electrophoresed on a 1.0% agarose gels as described in Example 18. The DNA was then depurinated and transferred to the membrane samples by capillary action using a neutral buffer system. The conditions for neutral transfer, probe preparation, hybridization, and autoradiography were identical to those described in Example 18. The DNA blotting results are presented in FIG. 2.

Figure 3:
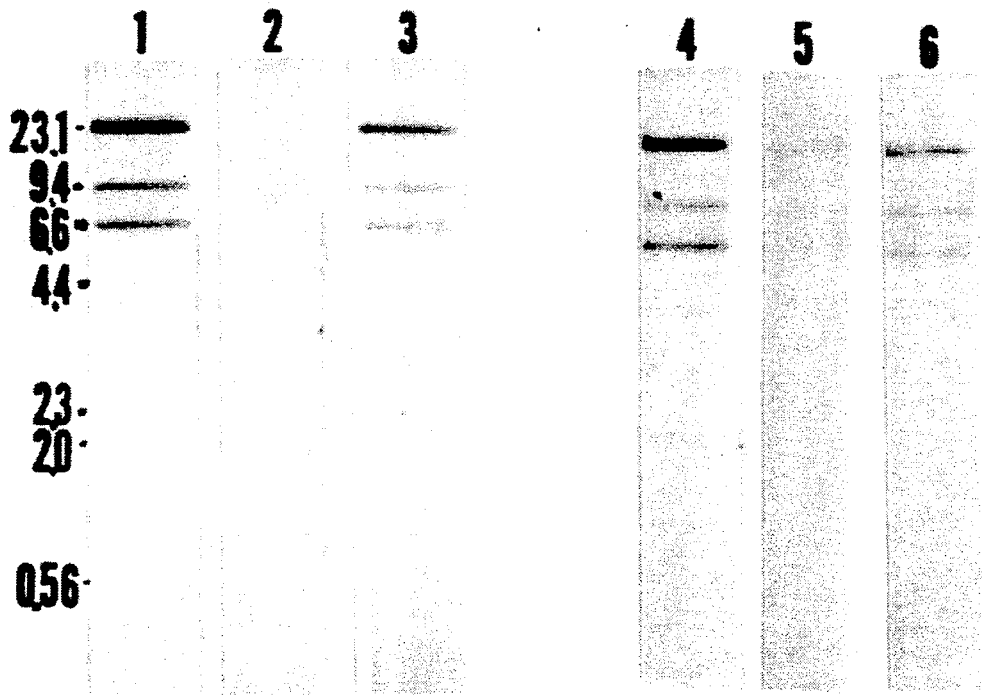
FIG. 3 is an autoradiogram comparing a charged nylon membrane to a charged polyethersulfone membrane in DNA hybridization/reprobing applications. Lanes 1, 2 and 3 were associated with a cationically charged polyethersulfone membrane and lanes 4, 5 and 6 were associated with a charged nylon membrane; DNA loading was 0.1 μg per lane. Autoradiographs of the membrane strips were taken after primary hybridization (lanes 1 and 4), extended probe removal (lanes 2 and 5) and secondary hybridization (lanes 3 and 6).

EXAMPLE 20 - Suitability of Cationically Charged Membranes in Reprobing Applications Since the ability of a membrane to retain DNA during the probe stripping process is critical, the "reprobability" of the membrane made in Example 9 and the charged nylon membrane (Genescreen Plus ®) were assessed in this example. The reprobing process was carried out as follows: (1) Lambda DNA, Hind III digest (0.1 μg/ lane) was electrophoresed on a 0.8% agarose gel as described in Example 18. The DNA was depurinated as described before and transferred to the membrane samples using a vacuum blotter (Transvac, Hoefer Scientific, San Francisco, Calif.). The methods for probe preparation, hybridization, washing and autoradiography were identical to those described in Example 18; (2) removal or "stripping" of the probe was performed by the alkaline method. A typical stripping procedure involves incubating the membrane samples in 0.4N NaOH at 42° C. for 30 minutes. To simulate 14 stripping cycles, the membrane samples in this test were incubated in 0.4N NaOH at 42° C. for 7 hours. Following the extended stripping cycle, the membrane samples were exposed to Kodak AR film to verify the loss of the probe and subsequently rehybridized with a radio labelled probe to detect DNA which remained bound to the membrane samples. The results obtained from the assay stated above are shown in FIG. 3 and demonstrate that the cationically charged polyethersulfone membrane is suitable for DNA reprobing applications.

Figure 4:
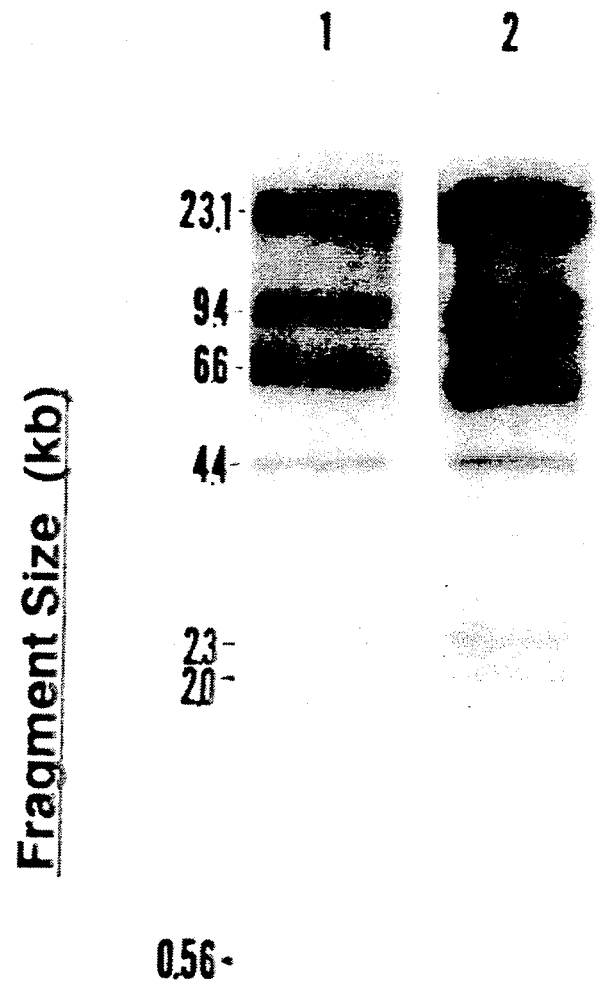
FIG. 4 is an autoradiogram comparing a non-aged charged polyethersulfone membrane and an aged charged polyethersulfone membrane in Southern blot performance.

EXAMPLE 21 - Effects of Aging on DNA Blotting Performance of the Cationically Charged Polyethersulfone Membrane In this example, the membrane made in Example 9 and the same membrane which had been baked at 56° C. for 60 days were used in the Southern Blot analysis to compare the blotting performance. In the actual assay, 0.1 μg of lambda DNA, Hind III digest was electrophoresed on a 1% agarose gel using the same buffer system as described in Example 18. The DNA was then depurinated and transferred to the membrane samples under alkaline conditions using a vacuum apparatus. The subsequent processes such as probe preparation, hybridization, washing and autoradiography were similar to those described in Example 18. The results of DNA blotting to cationically charged polyethersulfone membranes are illustrated in FIG. 4 and showed that aging had no effect on the Southern Blot performance.

We claim:

1. A cationic charge modified microporous hydrophilic membrane, comprising:
   a microporous membrane substrate comprising polyethersulfone and at least one non-leachable polymeric additive selected from polyvinylpyrrolidone and polyethylene glycol, which additive enhances hydrophilicity and has functional groups latently reactive with respective groups of charge modifying agents; and
   a primary charge modifying agent comprising polyethyleneimine-epichlorohydrin resin which contains polyamines, can chemically react with electrophile-containing compounds and thus impart a net positive charge, and is chemically grafted to said polymeric additive.

2. A membrane according to claim 1 where the polyethersulfone has the formula

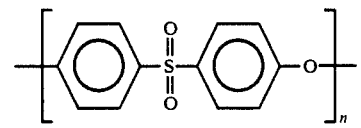

and the membrane substrate contains said additive in an amount effective to make the charge modified membrane when formed and dried inherently water wettable.

3. A process for preparing a cationic charge modified microporous hydrophilic membrane according to claim 1 comprising:
   A. providing a microporous membrane substrate comprising polyethersulfone and at least one non-leachable polymeric additive selected from polyvinylpyrrolidone and polyethylene glycol, which additive confers hydrophilicity and has functional groups latently reactive with reactive groups of charge modifying agents;
   B. reacting the membrane substrate with a primary charge modifying agent comprising polyethyleneimine-epichlorohydrin resin in an amount conferring a positive fixed formal charge to said membrane substrate; and
   C. washing and drying the resulting charge modified membrane.

4. A process according to claim 3 wherein the polyethersulfone has the formula

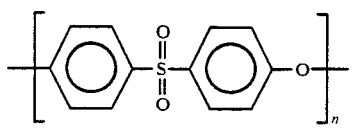

and the membrane substrate contains said additive in an amount effective to make the charge modified membrane when formed and dried inherently water wettable.

5. A process according to claim 3 where the charge modifying agent comprises polyethyleneimine-epichlorohydrin resin having the formula

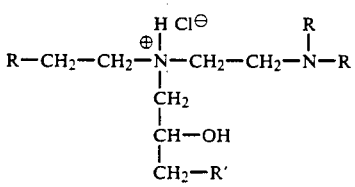

where R represents hydrogen or a continuation of the polyamine chain and R' represents —OH or —Cl.

6. A method of transferring a biological sample to an immobilizing matrix, comprising applying the sample to a charge modified membrane according to claim 1.

7. The method recited in claim 6, wherein the biological sample is mixed with a gel and the applying step comprises gel blotting.

8. The method recited in claim 6, wherein the applying comprises spot-wetting the biological sample to the membrane.

9. The method recited in claim 6, wherein the transferring step comprises electro-transfer of the biological sample to the membrane.

10. The method recited in claim 6, wherein the transferring step comprises capillary-transfer of the biological sample to the membrane.

11. The method recited in claim 6, wherein the membrane comprises polyethersulfone.

12. The method recited in claim 6, wherein the biological sample comprises bacteria.

13. The method recited in claim 6, wherein the biological sample comprises a macromolecule selected from the group consisting of DNA, RNA, and protein.

14. A method of identifying a macromolecule, comprising applying a biological sample which includes the macromolecule to a membrane according to claim 1; transferring the macromolecule to the membrane; and detecting the macromolecule.

15. The method recited in claim 14, wherein the applying step comprises spot-wetting the biological sample to the membrane.

16. The method recited in claim 14, wherein the applying step comprises gel blotting.

17. The method recited in claim 14, wherein the macromolecule is transferred by capillary action.

18. The method recited in claim 14, wherein the macromolecule is transferred by applying an electrical current to the biological sample.

19. The method recited in claim 14, wherein the detecting step is accomplished by ELISA.

20. A dot-blot method, comprising applying a biological sample, which includes a macromolecule selected from the group consisting of DNA, RNA, and protein to a membrane according to claim 1; and transferring the macromolecule to the membrane.

21. The method recited in claim 20 additionally comprising detecting the macromolecule.

22. A method of colony hybridization, comprising applying a biological sample comprising bacteria to a membrane according to claim 1; transferring the bacteria to the membrane; and detecting the bacteria on the membrane.

23. A cationic charge modified microporous hydrophilic membrane, comprising:

a microporous membrane substrate comprising polyethersulfone and at least one non-leachable active polymeric additive selected from polyvinylpyrrolidone and polyethylene glycol, which additive enhances hydrophilicity and has functional groups latently reactive with reactive groups of charge modifying agents;

a primary charge modifying agent comprising polyethyleneimine-epichlorohydrin resin which contains polyamines, can chemically react with electrophile-containing compounds and thus impart a net positive charge, and is chemically grafted to said polymeric additive; and a secondary charge modifying agent containing functionality that is reactive with the primary charge modifying agent, selected from the group consisting of partially phosphinated polyvinylbenzyl chloride ammonium and sulfonium analogs thereof, and quaternized poly(dimethylamine-co-epichlorohydrin) said secondary agent being reacted with the primary agent in an amount either such that the magnitude of the final formal positive charge is increased over that due to its reaction with the primary agent or such that the sensitivity of the primary agent to the variance of environmental pH is decreased.

24. A membrane according to claim 23 where the polyethersulfone has the formula

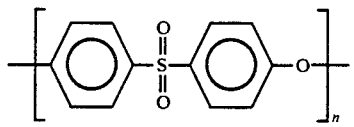

and the medium contains said additive in an amount effective to make the charge modified membrane when formed and dried inherently water wettable.

25. A membrane according to claim 23 where the primary charge modifying agent comprises polyethyleneimine-epichlorohydrin resin having the formula

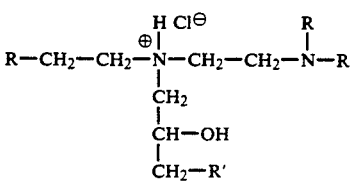

where R represents hydrogen or a continuation of the polyamine chain and R' represents —OH or —Cl.

26. A membrane according to claim 23 where the secondary charge modifying agent comprises a partially phosphinated polyvinylbenzyl chloride having the formula

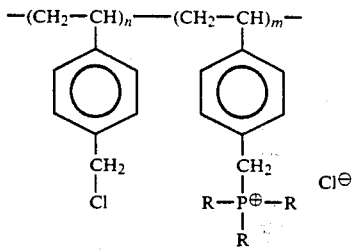

where m and n are integers indicating the polymer length and R is independently selected from lower alkyl and aryl groups; or an ammonium or sulfonium analog of said phosphinated benzyl chloride.

27. A membrane according to claim 23 where the secondary charge modifying agent comprises a quaternized poly(dimethylamine-co-epichlorohydrin) having the formula

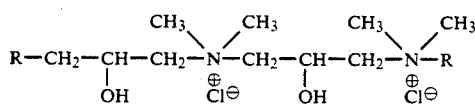

where R is a continuation of the polymer chain.

28. A process for preparing a cationic charge modified membrane according to claim 23 comprising:
A. providing a microporous membrane substrate comprising polyethersulfone and at least one non-leachable polymeric additive selected from polyvinylpyrrolidone and polyethylene glycol, which additive confers hydrophilicity and has functional groups latently reactive with reactive groups of charge modifying agents;
B. reacting the membrane substrate with a primary charge modifying agent comprising polyethyleneimine-epichlorohydrin resin in an amount conferring a positive fixed formal charge to said membrane substrate;
C. reacting the primary charge modifying agent with a secondary charge modifying agent containing functionality that is reactive with the primary charge modifying agent, selected from partially phosphinated polyvinylbenzyl chloride, ammonium and sulfonium analogs of said phosphinated benzyl chloride, and quaternized poly(dimethylamine-co-epichlorohydrin), said secondary agent being reacted with the primary agent in an amount either such that the magnitude of the final formal positive charge is increased over that due to its reaction with the primary agent or such that the sensitivity of the primary agent to the variance of environmental pH is increased; and
D. washing and drying the resulting charge modified membrane.

29. A process according to claim 28 where the polyethersulfone has the formula

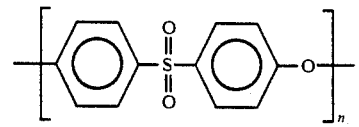

where n is an integer in the range from 50 to 150, and the medium contains said additive in an amount effective to make the charge modified membrane when formed and dried inherently water wettable.

30. A process according to claim 28 where the primary charge modifying agent comprises polyethyleneimine-epichlorohydrin resin having the formula

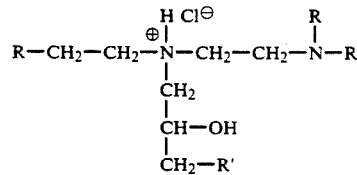

where R represents hydrogen or a continuation of the polyamine chain and R' represents —OH or —Cl.

31. A process according to claim 28 where the secondary charge modifying agent has the formula

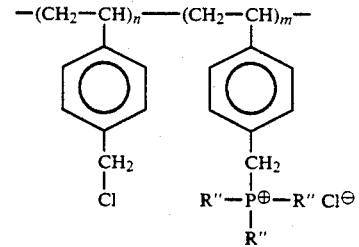

where R'' is independently selected from lower alkyl and aryl groups; or an ammonium or sulfonium analog of said phosphinated benzyl chloride.

32. A process according to claim 28 where the secondary charge modifying comprises a quaternized poly(dimethylamine-co-epichlorohydrin) having the formula

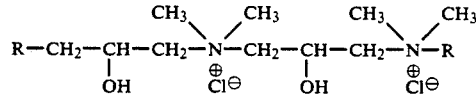

where R is a continuation of the polymer chain.

33. A blotting composition, comprising a sample substrate applied to a charge modified membrane according to claim 1 having an internal surface area and an external surface area, wherein substantially all available surfaces of the membrane are charge modified.

34. The blotting composition as recited in claim 33, wherein the sample substrate comprises a gel.

35. The blotting composition as recited in claim 33, wherein the sample substrate comprises a gel comprising macromolecules selected from the group consisting of DNA, RNA, and proteins.

36. The blotting composition as recited in claim 33, wherein the sample substrate comprises a gel which comprises macromolecules electrophoretically separated into a series of bands.

37. The blotting composition as recited in claim 33, wherein the sample substrate comprises materials capable of being bound by the fixed formal charge of the membrane.

38. The blotting composition as recited in claim 37, wherein said materials comprise amine-containing materials.

* * * * *

UNITED STATES PATENT AND TRADEMARK OFFICE
CERTIFICATE OF CORRECTION

PATENT NO. : 5,151,189

DATED : September 29, 1992

INVENTOR(S) : Hu et al.

It is certified that error appears in the above-identified patent and that said Letters Patent is hereby corrected as shown below:

Column 7, line 55, sentence missing and should be inserted -- The membrane sample was prewetted in ethanol prior to water bubble point and water flow rate tests--;

Column 15, line 35, delete "applying comprises" and insert --applying step comprises--.

Signed and Sealed this

Twelfth Day of October, 1993

Attest:

BRUCE LEHMAN

Attesting Officer

Commissioner of Patents and Trademarks